United States Patent [19]
Olander

[11] 4,221,735
[45] Sep. 9, 1980

[54] COMPLEXED MANGANESE CATALYST

[75] Inventor: Walter K. Olander, Clifton, N.Y.

[73] Assignee: General Electric Company, Pittsfield, Mass.

[21] Appl. No.: 880,134

[22] Filed: Feb. 22, 1978

Related U.S. Application Data

[62] Division of Ser. No. 753,501, Dec. 21, 1976, Pat. No. 4,093,596.

[51] Int. Cl.² .............................................. C07F 13/00
[52] U.S. Cl. .............................. 260/429 C; 260/429 J
[58] Field of Search ........................ 260/429 J, 429 C

[56] References Cited

U.S. PATENT DOCUMENTS

| | | | |
|---|---|---|---|
| 2,116,913 | 5/1938 | Schmidt et al. | 260/429 J |
| 3,248,410 | 4/1966 | Berenbaum | 260/429 J |

*Primary Examiner*—Lester L. Lee
*Attorney, Agent, or Firm*—Morgan, Finnegan, Pine, Foley & Lee

[57] ABSTRACT

A novel catalyst system is disclosed that is useful in the polymerization of polyphenylene oxide resins. The catalysts are manganese complexes that are derived from a manganese salt and an imine compound.

12 Claims, No Drawings

COMPLEXED MANGANESE CATALYST

This is a division of application Ser. No. 753,501 filed Dec. 21, 1976, now U.S. Pat. No. 4,093,596.

This invention is concerned with a novel catalyst that is useful for the polymerization of polyphenylene oxide resins. The catalysts are manganese complexes that are derived from a manganese salt and an imine compound.

BACKGROUND OF THE INVENTION

The polyphenylene oxides and methods for their preparation are known in the art. Many types of catalysts have been employed in the preparation of these polymers including copper and manganese based catalysts. Manganese based catalysts for the oxidative coupling of phenolic monomers in the formation of polyphenylene oxides are disclosed in McNelis, U.S. Pat. No. 3,220,979; Nakashio, U.S. Pat. No. 3,573,257; Nakashio, U.S. Pat. No. 2,787,361 and Olander, U.S. Pat. No. 3,956,272. In the applicant's copending applications Ser. No. 491,475 filed July 24, 1974 and Ser. No. 534,903 filed Dec. 20, 1974, there are disclosed novel procedures for polymerizing polyphenylene oxides with complex manganese based catalysts. All of these patents and applications are hereby incorporated by reference.

The manganese complexes of the prior art are good catalysts for the oxidative coupling of phenolic monomers in the preparation of polyphenylene oxide resins. These catalysts however tend to be thermally unstable and it is usually necessary to control the reaction temperature at a level that does not cause deactivation of the catalyst. It has now been found that a novel class of manganese based complexes derived from a manganese salt and an imine compound may be employed in the preparation of polyphenylene oxides under process temperatures that are higher than the temperatures usually employed with prior art manganese complexes.

The prior art complexes have included complexes that were prepared from manganese salts and an amine. In U.S. Pat. No. 3,787,361, a catalyst was prepared from an alkanolamine and manganese chloride. Other catalysts have been prepared from manganese salts and an imine that contains this groups and is derived from an unsaturated alkanolamine as described in Japanese patent publication No. 28680/74.

Accordingly, it is a primary object of this invention to provide a novel manganese catalyst for the oxidative coupling of phenolic monomers.

It is also an object of this invention to provide manganese catalyst for the oxidative coupling of phenolic monomers which has improved thermal stability.

DETAILED DESCRIPTION OF THE INVENTION

The present invention provides a novel catalyst for the oxidative coupling of phenolic monomers. The novel catalyst is a compound of the formula:

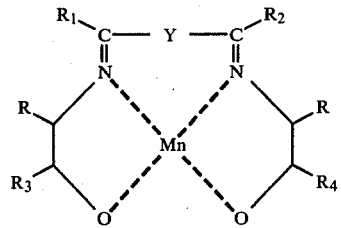

wherein $R_1$, $R_2$, $R_3$ and $R_4$ are independently selected from the group consisting of lower alkyl of from 1 to 8 carbon atoms, aryl and hydrogen; $R_1$ and $R_2$ may be concatenated together when Y is a single bond to form a six carbon ring that may be saturated or have up to two double bonds and which may be substituted with a substituent selected from the group consisting of hydrogen, halogen, lower alkyl of from 1 to 8 carbon atoms, lower alkoxy of from 1 to 8 carbon atoms. Y is a single bond or is $CR_5R_6$ where $R_5$ and $R_6$ are independently selected from the group consisting of hydrogen, lower alkyl of 1 to 8 carbon atoms and aryl. R is hydrogen or R may be concatenated together with $R_3$ or $R_4$ to form a saturated ring containing 5 or 6 carbon atoms or an unsaturated ring containing 5 or 6 carbon atoms which may be unsubstituted or substituted with lower alkyl groups of 1 to 8 carbon atoms or aryl groups.

As used herein and in the appended claims lower alkyl is used to describe saturated straight and branched chain hydrocarbon groups such as methyl, ethyl, n-propyl, i-propyl, n-butyl, n-hexyl and the like. The term aryl is employed to include phenyl and naphthyl. The term halogen is employed to include chlorine, bromine, iodine and fluorine. The term lower alkoxy is employed to include methoxy, ethoxy, n-propoxy, n-hexoxy and the the like. The term saturated ring containing 5 or 6 carbons includes cyclopentyl and cyclohexyl. The term unsaturated ring containing 5 or 6 carbon atoms which may be unsubstituted or substituted with lower alkyl groups of 1 to 8 carbon atoms or with aryl groups included cyclopentenyl, phenyl, 4-methylphenyl, 4-n-butylphenyl, 5-phenylphenyl and the like.

The novel manganese based catalysts include compounds of the formula:

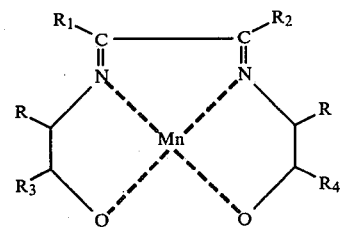

wherein $R_1$, $R_2$, $R_3$, $R_4$ and R are the same as hereinabove defined.

The preferred catalysts of this type are those wherein $R_1$ and $R_2$ are methyl or phenyl and $R_3$ and $R_4$ are phenyl. In addition the manganese based catalysts also include compounds of the formula:

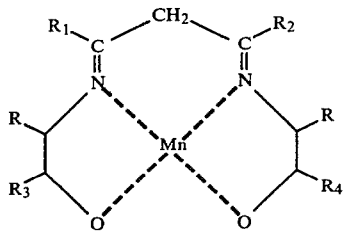

wherein $R_1$, $R_2$, $R_3$, $R_4$ and R are the same as hereinabove defined.

The preferred catalysts are those wherein $R_1$ and $R_2$ are methyl or phenyl and $R_3$ and $R_4$ are methyl, hydrogen or phenyl.

Manganese based catalysts of the formula:

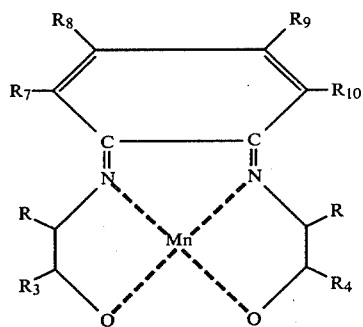

wherein R, $R_3$ and $R_4$ are the same as hereinabove defined and $R_7$, $R_8$, $R_9$ and $R_{10}$ are independently selected from the group consisting of hydrogen, halogen, lower alkyl of from 1 to 8 carbon atoms and lower alkoxy of from 1 to 8 carbon atoms.

The manganese based catalysts of the invention may be employed to catalyze the oxidative coupling of a phenolic monomer of the formula:

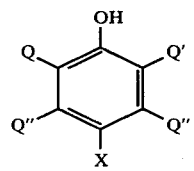

wherein X is a substituent selected from the group consisting of hydrogen, chlorine, bromine and iodine, Q is a monovalent substituent selected from the group consisting of hydrocarbon radicals, halohydrocarbon radicals having at least two carbon atoms between the halogen atom and the phenol nucleus, hydrocarbonoxy and halohydrocarbonoxy radicals having at least two carbon atoms between the halogen atom and the phenol nucleus; and Q' is as defined for Q, and in addition may be halogen and Q" are each as defined for Q' and in addition hydrogen with the provision that Q, Q' and Q" are all free of a tertiary carbon atom.

The preferred phenolic monomer is 2,6-xylenol.

The imine employed to form manganese based catalysts of the invention may be prepared by reacting an appropriate di-ketone with a primary alkanolamine according to the following reaction:

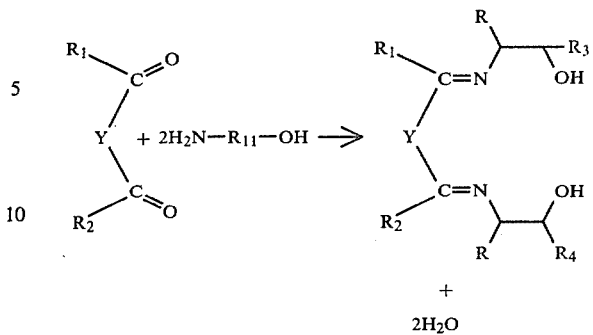

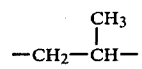

wherein $R_1$, $R_2$, $R_3$, $R_4$ and R are the same as hereinabove defined; $R_{11}$ is lower alkylene of 2-4 carbon atoms, phenyl substituted lower alkylene of 2-4 carbon atoms, o-phenylene, o-phenylene substituted with lower alkyl groups of from 1 to 8 carbon atoms or aryl, or o-cyclohexylene. As used herein the term lower alkylene of from 2 to 3 carbon atoms includes —CH$_2$—CH$_2$—; —CH$_2$—CH—CH$_2$—; —CH$_2$—CH$_2$—CH$_2$—;

$$-CH_2-\underset{\underset{CH_3}{|}}{CH}-$$

and the like.

Generally the imine may be prepared by heating the di-ketone with the primary alkanolamine in an appropriate solvent i.e., benzene or a lower alkanol of 1–6 carbon atoms such as methanol. Usually it is preferred to employ a water removing means so that the water of reaction is separated from the reaction product. If desired the manganese salt may be added after the imine is prepared or the manganese salt, the di-ketone and the primary alkanolamine may all be combined to form the manganese imine chelate.

Generally it is preferred to employ substantially stoichiometric amounts of the chelate forming materials although it may be desirable to utilize an excess of the imine forming components to insure substantially complete chelation of the manganese salt.

The suitable manganese salts are the manganese (II) halides such as manganese (II) chloride (also known as manganous chloride) manganese (II) bromide, manganese (II) iodide, etc., as well as other manganese (II) compounds such as manganese carbonate, manganese (II) oxalate, manganese (II) sulfate, manganese (II) acetate, manganese (II) nitrate, manganese (II) phosphates, etc., including hydrated forms thereof. Manganese (VII) in the form of potassium permanganate may be employed.

The chelate compounds may be formed by reacting substantially stoichiometric amounts of the manganese (II) salt and the amine in the presence of a suitable solvent such as a lower alkanol of 1 to 6 carbon atoms such as methanol. Two moles of a base such as sodium hydroxide, may be employed per mole of manganese in order to promote complex formation.

The imine may be formed from primaryamino alkanols having a 1,2-amino-alcohol or a 1,3-amino-alcohol configuration. Suitable amino-alcohols include ethanolamine; 1-amino-isopropanol; 2-amino-1-phenylethanol; o-aminophenol and the like.

The diketones include 2,4-pentanedione; di-benzoylmethane; benzil; 2,3-butanedione; o-benzoquinone and the like.

The process in which the novel manganese based catalyst may be employed to catalyze the oxidative coupling of phenolic monomers may be carried out by combining the catalyst and monomer in an appropriate organic solvent in the presence of an oxygen containing gas and alkali. Generally, polymerizations may be carried out using a mole ratio of phenolic monomer to manganese of from 100:1 to 200:1. A phenolic monomer such as 2,6-xylenol is dissolved in appropriate organic solvent such as toluene or chlorobenzene at a weight percent concentration within the range of 20:80 to about 5:95, preferably 15:85 to 10:90 of phenolic monomer to organic solvent.

The polymerization is initiated by introducing a stream of oxygen at a rate that is sufficient to be in excess over that which is absorbed. The alkali is preferably added as a 50% aqueous solution of sodium hydroxide sufficient to maintain a mole ratio of 14:1 to 18:1 and more preferably 16:1 of phenolic compound to hydroxide ion during the polymerization reaction. Other basic materials are described in U.S. Pat. No. 3,956,242. When a polyphenylene oxide having an intrinsic viscosity of about 0.45 dl/g as measured in chloroform at 30° C. is obtained, the reaction may be terminated by adding to the reactor, sufficient aqueous acetic or sulfuric acid to neutralize the reaction media. After neutralization, the entire reaction mixture may be precipitated with a suitable solvent, e.g., methanol and isolated according to standard techniques.

Polymerizations may be carried out in the presence of primary, secondary or tertiary amines in a minor amount. The presence of an amine in the reaction tends to yield a polymer having a lighter color. The use of amines will also have an affect on the reaction rates and the physical properties of the product. If an amine is employed, it may be utilized at a level of from 1 mole of amine to 70-100 moles of phenolic monomer. Suitable amines include mono and di-alkyl amines having from 1 to 10 carbon atoms such as n-butyl amine, n-hexyl amine, di-n-hexyl amine and the like. Other amines may be selected from the amines that are disclosed in U.S. Pat. No. 3,306,874 and U.S. Pat. No. 3,306,875, both of which are hereby incorporated by reference.

DESCRIPTION OF THE PREFERRED EMBODIMENTS

The following examples illustrate the process of this invention. They are merely illustrative and are not to be construed to limit the invention in any manner whatsoever.

EXAMPLE I

A reaction vessel was charged with 10.0 g 2,4-pentanedione (0.1 mole) and 12.82 g of 95% ethanolamine (0.2 mole) in benzene and the reaction mixture was refluxed for several hours. Water amounting to 58% of theoretical was collected in an attached Dean-Stark trap. The crude 2,4-pentane-diethanolimine was isolated as a tacky solid after adding hexane and concentrating the resulting solution.

Using the crude 2,4-pentane-diethanolimine, the following polymerization was undertaken. Based on a total recharge, the following materials were weighed out:
 toluene: 360 g (413 ml)
 methanol: 60 g (71 ml)
 2,6-xylenol: 80 g (16% solids)
 sodium hydroxide (50% aq.): 3.2 g
 n-hexylamine: 1.0 g
 $MnCl_2$: 0.8251 g
 crude, 2,4-pentane-diethanolimine: 1.1409 g The toluene, 2,6-xylenol and most of the methanol were combined in a one liter reactor oxygen was added at 1.0 SCFH. The catalyst in methanol, base in methanol and n-hexylamine in toluene were charged into the reactor in that order. An immediate exotherm followed which was controlled more or less isothermally at 28° C. The reaction was terminated after 2 hours with the addition of aqueous acetic acid and the polymer subsequently methanol precipitated. The intrinsic viscosity was 0.59 dl/g as measured in chloroform at 30° C.

EXAMPLE 2

A portion of the crude 2,4-pentanediethanolamine from Example I was recrystallized from diethyl ether yielding a white solid (m.p. 73° C.) which was employed in the following polymerization.

The general procedure of Example I was employed except that a 375 g charge was employed as follows:
 chlorobenzene: 255 g (232 ml)
 methanol: 60 g (75 ml)
 2,6-xylenol: 60 g (16% solids)
 sodium hydroxide: 2.4 g (50% aq. solution)
 n-hexylamine: 1.2 g
 $MnCl_2$: 0.3096 g
 2,4-pentanediethanolamine: 0.4575 g The polymerization was run for 2 hours at approximately 30° C. Thereafter the reaction was quenched with aqueous acetic acid and the poly(2,6-dimethyl-1,4-phenylene oxide) was isolated from the reaction mixture in accordance with standard procedures. The intrinsic viscosity of the polymer was 0.42 dl/g as measured in chloroform at 30° C.

EXAMPLE III

A mixture of 1.82 g of 2,4-pentanedione (0.0182) moles) and 5.0 g 2-amino-1-phenyl ethanol (0.0364) in 125 ml benzene was refluxed for about 4 hours during which time at least 62% of the theoretical amount of water expected was collected. The reaction mixture was taken to dryness and taken up in toluene to give 30 g of solution which was used directly. A 500 g charge was employed:
 toluene: 360 g (413 ml)
 methanol: 60 g (75 ml)
 2,6-xylenol: 80 g (16% solids)
 sodium hydroxide: 3.2 g (of 50% aq. solution)
 n-hexylamine: 1.0 g
 $MnCl_2$: 0.8251 g
 2,4-pentane (bis-2-imino-1-phenylethanol): 10.8 g (of toluene solution)

Using the general procedure of Example I, the polymerization was run for 2.25 hours and quenched with aqueous acetic acid. The intrinsic viscosity of the isolated polymer was 0.57 dl/g as measured in chloroform at 30° C.

EXAMPLE IV

A mixture of 10.0 g of 2,4-pentanedione (0.1 mole) and 22.94 g of 95% o-aminophenol (0.2 mole) was refluxed in benzene for approximately 24 hours. At least 78% of the theoretical amount of water was collected. On cooling, 2,4-pentane (bis-o- imino phenol) collected as a green crystalline solid that was used without further purification. A 700 g charge was employed:
- toluene: 490 g (562.5 ml)
- methanol: 98 g (122.5 ml)
- 2,6-xylenol: 112 g (16% solids)
- sodium hydroxide: 4.5 g (50% aq. solu.)
- n-hexylamine: 1.12 g
- $MnCl_2$: 1.1552 g
- 2,4-pentane (bis-o-imino phenol): 2.5887 g Using the general procedure of Example 1, the polymerization was run for 116 minutes at 25°–30° C. and was quenched with aqueous sulfuric acid. The intrinsic viscosity was 0.49 dl/g as measured in chloroform at 30° C.

EXAMPLE V

A mixture of 5.0 bis-benzoyl methane (0.022 mole) and 2.86 g of 95% ethanolamine (0.0446 mole) was refluxed overnight in toluene. The solvent was removed by entrainment with gaseous nitrogen and 1,3-diphenyl-1,3-propane diethanolamine was collected as a white solid (mp 88° C.) which was used directly. A 375 g charge was employed in the polymerization of 2,6-xylenol following the general procedure of Example 1:
- chlorobenzene: 259 g (235 ml)
- methanol: 60 g (75 ml)
- 2,6-xylenol: 60 g (16% solids)
- sodium hydroxide: 2.4 g (50% aq. solution)
- n-hexylamine: 1.2 g
- $MnCl_2$: 0.3096 g
- 1,3-diphenyl-1,3-propane diethanolimine: 0.7626 g The polymerization reaction was run for 2 hours at 25°–30° C. and quenched with aqueous acetic acid. The intrinsic viscosity of the poly(2,6-dimethyl-1,4-phenylene oxide) was 0.40 dl/g as measured in chloroform at 30° C.

EXAMPLE VI

A mixture of 2.0 g of Mn $(OAc)_2 \cdot 4H_2O$ (0.00816 moles) 0.7 g (0.00813 moles) of 2,3-butanedione and 100 ml of methanol are warmed to 60° C. and agitated for 30 minutes. The in situ condensation is effected by addition of 2.2 g (0.01603 moles) of 2-amino-1-phenylethanol and continued agitation for 30 minutes. The solution is neutralized by the addition of 0.6 g of 50% aqueous sodium hydroxide. The following materials were charged into a one liter reactor and a bulk polymerization carried out.
- toluene: 450 ml
- methanol: 50 ml
- 2,6-xylenol: 100 g
- sodium hydroxide: 4.0 g (50% aq.)
- catalyst solution: (as described above)

Oxygen was introduced at 1.0 SCFH, and the reaction temperature rose spontaneously and was maintained at 50° (using an internal cooling coil until insufficient monomer remained to support the exotherm at that level. The reaction is terminated at 54 minutes by adding acetic acid. The intrinsic viscosity of the poly(2,6-dimethyl-1,4-phenylene oxide) was 0.62 dl/g as measured in chloroform at 30° C.

EXAMPLE VII

The catalyst was prepared by combining 2.0 g of $Mn(OAc)_2 \cdot 4H_2O$ (0.00816 moles), 1.71 g of benzil (0.00814 moles) and 2.24 g 2-amino-1-phenylethanol (0.01633 moles) in 100 ml of methanol for one hour at 45° C. Thereafter, 0.64 g of 50% aq. sodium hydroxide (0.0080 moles) was employed to neutralize the acetic acid liberated by complex formation.

The catalyst solution prepared above was transferred to a one liter reactor containing the following:
- toluene: 502 ml
- methanol: 10 ml
- 2,6-xylenol: 100 g (0.8196 mole)
- sodium hydroxide: 4.0 g (50% aq. solu.)

Oxygen was introduced at 1.5 SCFH and a vigorous exothermic reaction follows which is terminated after 60 minutes. The intrinsic viscosity of the poly(2,6-dimethyl-1,4-phenylene oxide) is 0.52 dl/g as measured in chloroform at 30° C.

EXAMPLE VIII

A polymerization combining the following materials:
- toluene: 502 ml
- methanol: 110 ml
- 2,6-xylenol: 100 g (0.8196 moles)
- sodium hydroxide: 4.0 g (50% aq. solution)
- n-hexylamine: 1.0 g
- $MnCl_2$: 1.03 g
- benzil bis(ethanolimine): 1.0 g was undertaken as in Example 1.

The manganese (II) chloride and benzil bis(ethanolimine) are combined in a portion of the methanol and added to the reactor containing the previously charged solvent; 2,6-xylenol; base; amine and remaining methanol. The temperature was maintained between 25°–30° C. for 120 minutes, at which time the reaction is quenched with acetic acid. The methanol precipitated poly(2, 6-dimethyl-1, 4-phenylene oxide) has an intrinsic viscosity of 0.53 dl/g as measured in chloroform at 30° C.

EXAMPLE IX

A solution of 0.56 g 2,3-butanedione (0.00655 moles) and 1.80 g of 2-amino-phenylethanol (0.0131 moles) are refluxed 6 hours in 70 mls. of benzene. After stirring an additional 14 hours, 0.82 manganese (II) chloride (0.00655 moles) in 50 ml of methanol is added. The catalyst is added to the reactor containing:
- 2,6-xylenol: 160 g (1.311 moles)
- methanol: 70 ml
- toluene: 575 ml
- sodium hydroxide: 6.4 g (50% aq. solution)

and oxygenated at 1.5 SCFH. A reaction temperature of 43°–49° C. was maintained for 57 minutes at which time the reaction was terminated by addition of 50% aqueous acetic acid. The methanol precipitated poly(2,6-dimethyl-1,4-phenylene oxide) has an intrinsic viscosity of 0.54 dl/g as measured in chloroform at 30° C.

Although the above examples have shown various modifications of the present invention, other variations are possible in light of the above teachings. It is, therefore, to be understood that changes may be made in the particular embodiments of the invention described which are within the full intended scope of the invention as defined by the appended claim.

I claim:

1. A catalyst for the oxidative coupling of a phenolic monomer which consists of a compound of the formula:

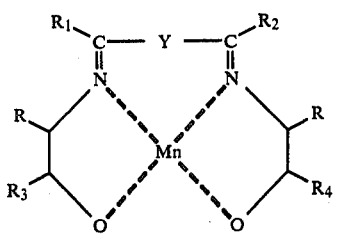

wherein $R_1$, $R_2$, $R_3$ and $R_4$ are independently selected from the group consisting of lower alkyl of from 1 to 8 carbon atoms, aryl and hydrogen; $R_1$ and $R_2$ may be concatenated together when Y is a single bond to form a six carbon ring that may be saturated or have up to two double bonds and which may be substituted with a substituent selected from the group consisting of hydrogen, halogen, lower alkyl of from 1 to 8 carbon atoms, lower alkoxy of from 1 to 8 carbon atoms; Y is a single bond or is $CR_5R_6$ wherein $R_5$ and $R_6$ are independently selected from the group selected consisting of hydrogen, lower alkyl of 1 to 8 carbon atoms and aryl; and R is hydrogen or R may be concatenated together with $R_3$ or $R_4$ to form an unsaturated ring containing 5 or 6 carbon atoms or a saturated ring containing 5 or 6 carbonatoms which may be unsubstituted or substituted with lower alkyl groups of 1 to 8 carbon atoms or aryl groups.

2. A catalyst as defined in claim 1 which consists of a compound of the formula:

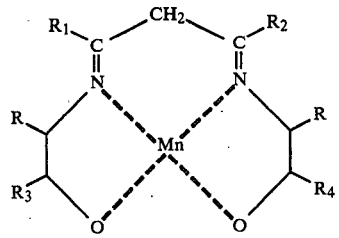

wherein $R_1$, $R_2$, $R_3$, $R_4$ and R are selected from the group consisting of lower alkyl of from 1 to 8 carbon atoms, aryl and hydrogen.

3. A catalyst as defined in claim 2 wherein $R_1$ and $R_2$ are methyl and R, $R_3$ and $R_4$ are hydrogen.

4. A catalyst as defined in claim 3 wherein $R_1$ and $R_2$ are phenyl.

5. A catalyst as defined in claim 2 wherein $R_1$, $R_2$, $R_3$ and $R_4$ are phenyl and R is hydrogen.

6. A catalyst as defined in claim 2 wherein $R_1$, $R_2$, $R_3$ and $R_4$ are methyl and R is hydrogen.

7. A catalyst as defined in claim 1 which consists of a compound of the formula:

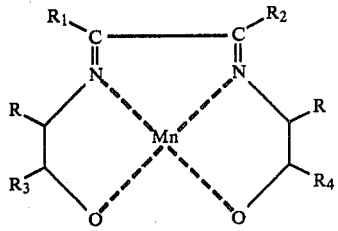

wherein $R_1$, $R_2$, $R_3$, $R_4$ and R are independently selected from the group consisting of lower alkyl of from 1 to 8 carbon atoms, aryl and hydrogen.

8. A catalyst as defined in claim 6 wherein $R_1$ and $R_2$ are methyl and $R_3$ and $R_4$ are phenyl and R is hydrogen.

9. A catalyst as defined in claim 6 wherein $R_1$, $R_2$, $R_3$ and $R_4$ are phenyl and R is hydrogen.

10. A catalyst as defined in claim 1 which consists of a compound of the formula:

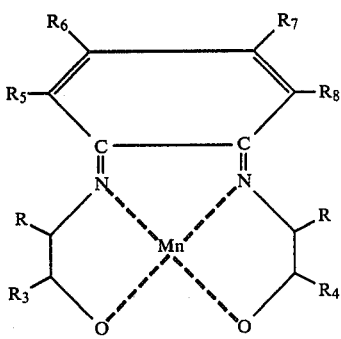

wherein $R_5$, $R_6$, $R_7$ and $R_8$ are independently selected from the group consisting of hydrogen, halogen, lower alkyl of from 1 to 8 carbon atoms and lower alkoxy of from 1 to 8 carbon atoms.

11. The catalyst of claim 9 wherein $R_3$, $R_4$, $R_5$, $R_6$, $R_7$ and $R_8$ are hydrogen and $R_3$ and $R_4$ are phenyl.

12. A catalyst composition which comprises a compound of claim 1 and methanol.

* * * * *

UNITED STATES PATENT AND TRADEMARK OFFICE
CERTIFICATE OF CORRECTION

PATENT NO. : 4,221,735
DATED : September 9, 1980
INVENTOR(S) : Walter K. Olander It is certified that error appears in the above—identified patent and that said Letters Patent is hereby corrected as shown below:

In Column 9, line 27, Claim 1, "bonatoms" should be --bon atoms--.

Signed and Sealed this

Seventeenth Day of February 1981

[SEAL]

*Attest:*

*Attesting Officer*

RENE D. TEGTMEYER

*Acting Commissioner of Patents and Trademarks*

UNITED STATES PATENT AND TRADEMARK OFFICE
CERTIFICATE OF CORRECTION

PATENT NO. : 4,221,735

DATED : September 9, 1980

INVENTOR(S) : Walter K. Olander

It is certified that error appears in the above—identified patent and that said Letters Patent is hereby corrected as shown below:

In Column 1, line 59, should read -- provide a manganese--

Signed and Sealed this

Eighteenth Day of August 1981

[SEAL]

Attest:

Attesting Officer

GERALD J. MOSSINGHOFF

Commissioner of Patents and Trademarks